United States Patent [19]

Du Bae

[11] 4,184,364
[45] Jan. 22, 1980

[54] VISCOSIMETER
[75] Inventor: Hyung Du Bae, Brea, Calif.
[73] Assignee: International Telephone and Telegraph Corporation, New York, N.Y.
[21] Appl. No.: 944,756
[22] Filed: Sep. 22, 1978
[51] Int. Cl.² .............................. G01N 11/02
[52] U.S. Cl. ............................ 73/54; 73/195
[58] Field of Search ............... 73/54, 231 R, 229, 195, 73/196

[56] References Cited
U.S. PATENT DOCUMENTS 3,710,622  1/1973  Hammond et al. ............ 73/231 R
4,067,230  1/1978  Ball ................................ 73/54

FOREIGN PATENT DOCUMENTS 1266994  4/1968  Fed. Rep. of Germany ......... 73/229
1804439  10/1970  Fed. Rep. of Germany ......... 73/229
45-36558  11/1970  Japan ............................ 73/54
882478  11/1961  United Kingdom ................ 73/196

Primary Examiner—Gerald Goldberg
Assistant Examiner—Joseph W. Roskos

[57]  ABSTRACT

A viscosimeter utilizing two different turbine flowmeters driven in series in a closed loop by a pump. It has been discovered that the viscosity v of the pumped fluid may be calculated from the expression $$v = Af_j - Bf_i + C$$

where
A, B and C are constants which may be determined by turbine flowmeter, viscosimeter or other analytical or empirical calibration, and
$f_i$ and $f_j$ are the pulse repetition frequencies at the outputs of the respective turbine flowmeters.

11 Claims, 3 Drawing Figures

VISCOSIMETER

BACKGROUND OF THE INVENTION

This invention relates to the art of detecting fluid properties, and more particularly to a viscosimeter or the like.

PRIOR ART STATEMENT

It has been known in the art to use two rotors in a common pipe section to measure viscosity. However, the calibration of such an instrument is quite complicated. See column 7, lines 41-46, of U.S. Pat. No. 3,735,637 issued May 29, 1973. Moreover, one of the prior art rotors is feathered. It is therefore not a true turbine flowmeter.

According to the foregoing, the phrase "turbine flowmeter" is hereby defined for use herein and in the claims to mean a turbine having a rotor with blades of a finite pitch (larger than zero) i.e., larger than that when feathered or parallel to the flow direction.

SUMMARY OF THE INVENTION

In accordance with the viscosimeter of the present invention, the above-described and other disadvantages of the prior art are overcome by providing two different turbine flowmeters driven in series by a pump, and computer means to calculate viscosity as a function of the rotor speeds.

BRIEF DESCRIPTION OF THE DRAWINGS

In the accompanying drawings which illustrate exemplary embodiments of the present invention.

DESCRIPTION OF THE PREFERRED EMBODIMENTS

Figure 1:
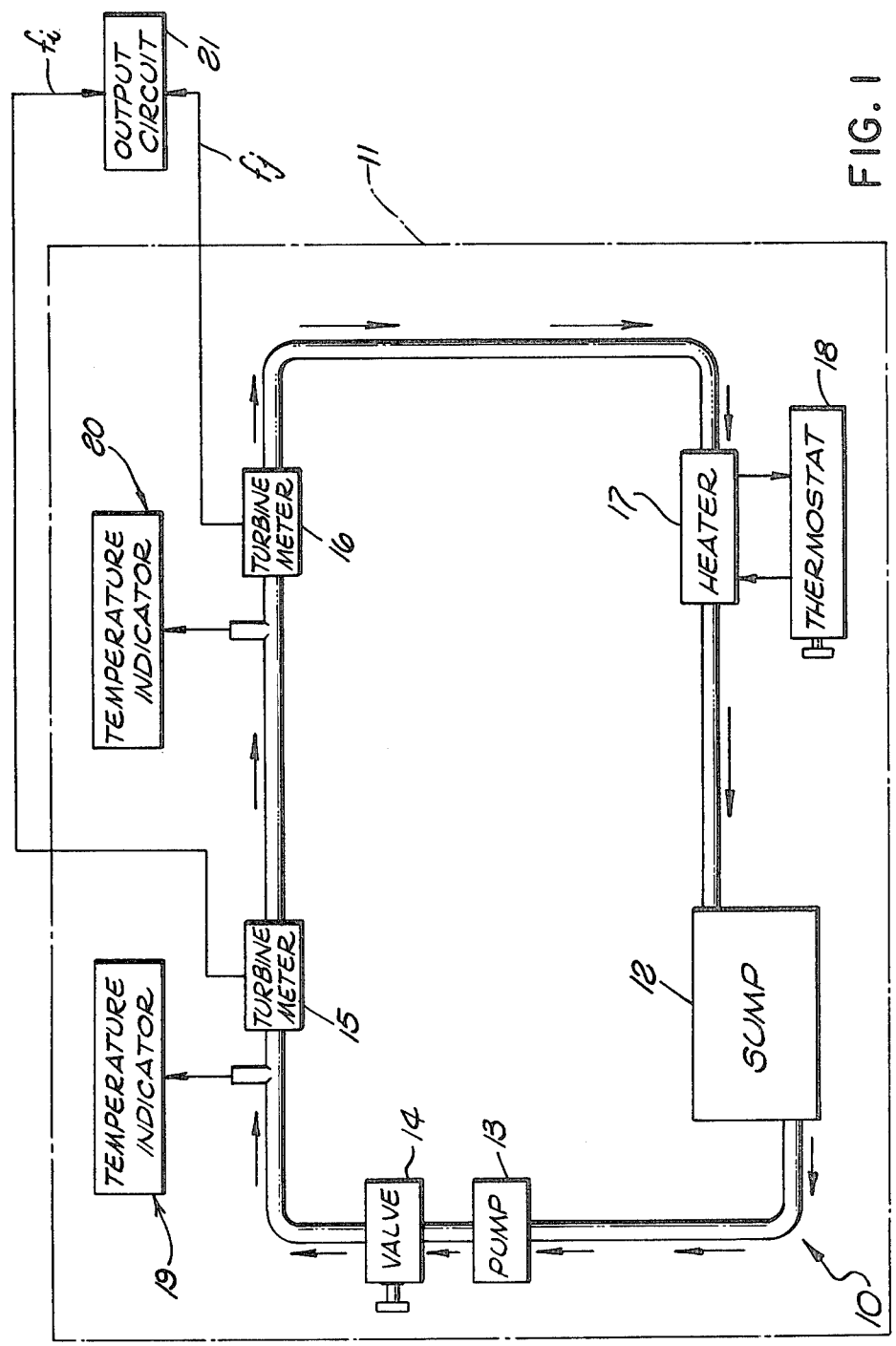
FIG. 1 is a diagrammatic view of a viscosimeter constructed in accordance with the present invention.

In FIG. 1, preferably a closed loop 10 is insulated at 11. A pump 13, a manually adjustable valve 14, a first turbine flowmeter 15, a second turbine flowmeter 16, and a heater 17 are connected in series in that order, pump 13 being connected from a sump 12, and heater 17 being connected back to sump 12 to complete loop 10.

If desired, the temperature of a fluid flowing in loop 10 and circulated therethrough by pump 13 may be maintained approximately constant by a manually adjustable thermostat 18.

Fluid temperature may be checked by conventional probes 19 and 20.

Each individual block shown in FIG. 1 except an output circuit 21 may, by itself, be entirely conventional, but not the combinations thereof.

Turbine flowmeters 15 and 16 are different and produce output pulses at frequencies $f_i$ and $f_j$, respectively, such that respective volume flow rates $Q_i$ and $Q_j$ therethrough are $$Q_i = m_1 f_i + n_1 v + c_1 \quad (1)$$

$$Q_j = m_2 f_j + n_2 v + c_2 \quad (2)$$

$$Q_i = Q_j \quad (3)$$

where $m_1$, $n_1$, $c_1$, $m_2$, $n_2$ and $c_2$ are constants, and v is the viscosity of the fluid in the loop 10.

The constant of equations (1) and (2) are determined by the operating characteristics of turbine flowmeters 15 and 16, respectively. The viscosimeter of FIG. 1 may thus be calibrated by calibrating each turbine meter individually or calibrating the entire assembly. Either calibration may be performed analytically or empirically.

At any rate, the condition $$n_1 \neq n_2 \quad (4)$$

must be met, or viscosity becomes independent of all constants and variables and cannot be calculated.

More often than not, the following conditions will, although need not necessarily, exist $$m_1 \neq m_2 \quad (5)$$

$$c_1 \neq c_2 \quad (6)$$

In other words, turbine flowmeters 15 and 16 typically have different sizes, and have different operating characteristics.

Turbine flowmeters 15 and 16 each are of the conventional type which produces output voltage or current pulses at a rate proportional to the respective corresponding volume rate of fluid flow therethrough. See the $f_i$ and $f_j$ inputs to output circuit 21 in FIG. 1.

Changing $Q_j$ to $Q_i$ in equation (2) [see (3)], and subtracting equation (2) from equation (1), it is possible to solve for v thus $$v = A f_j - B f_i + C \quad (7)$$

where $$A = m_2/(n_1 - n_2) \quad (8)$$

$$B = m_1/(n_1 - n_2) \quad (9)$$

$$C = (c_2 - c_1)/(n_1 - n_2) \quad (10)$$

All the constants of equation (7) may be determined empirically with the use of a known calibration fluid, if desired.

Figure 2:
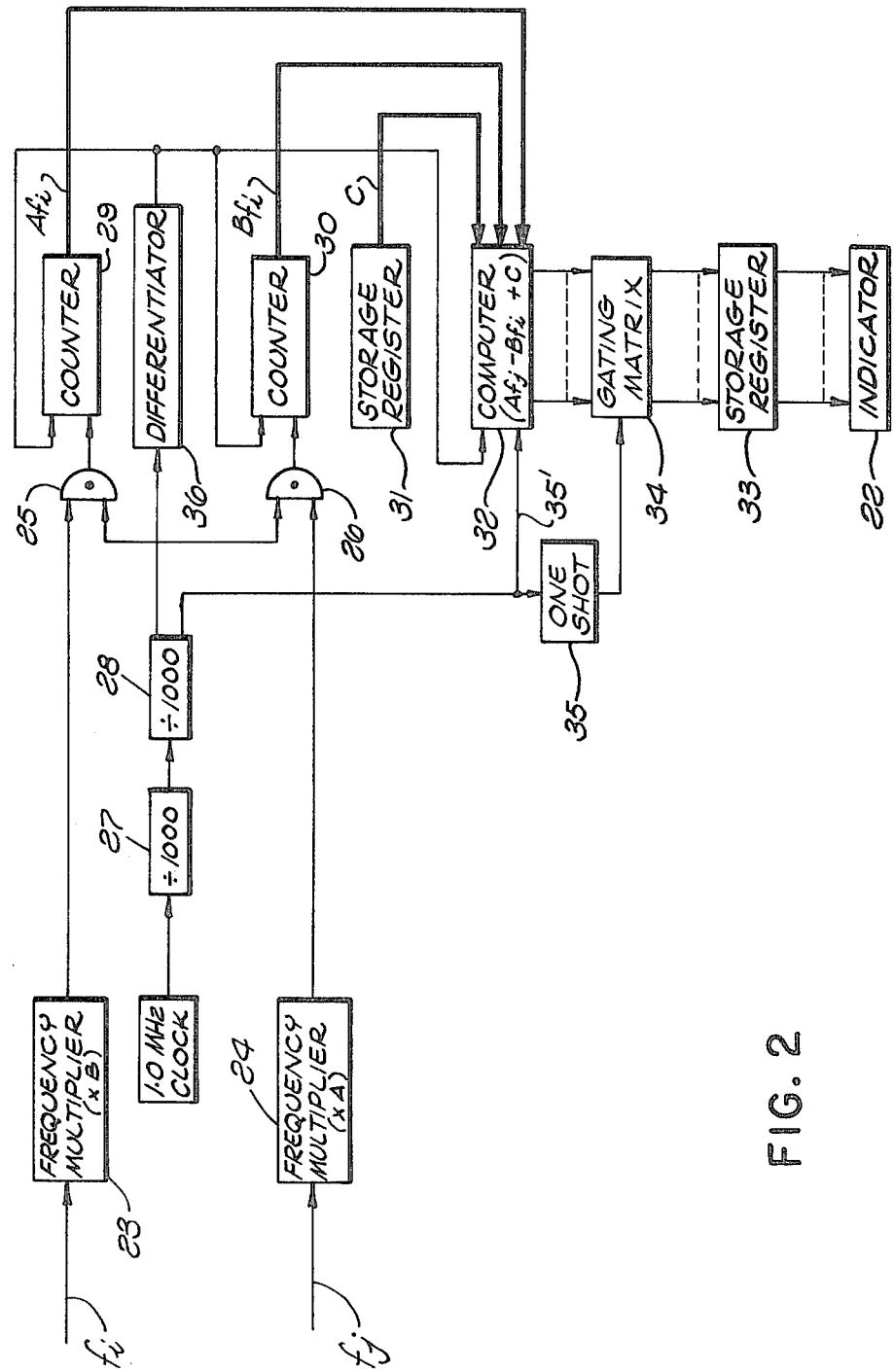
FIG. 2 is a block diagram of an output circuit shown in FIG. 1.

Output circuit 21 in FIG. 1 is shown in more detail in FIG. 2. Essentially, output circuit 21 computes equation (7), but may supply a viscosity signal to a process controller, an indicator 22 or otherwise.

Conventional optional frequency multipliers are provided at 23 and 24 to receive pulses $f_i$ and $f_j$, respectively. A 1.0 MHz clock supplies a 1.0 second gate simultaneously to AND gates 25 and 26, through dividers 27 and 28, AND gates 25 and 26 also being connected from the outputs of frequency multipliers 23 and 24, respectively.

Counters 29 and 30 store counts proportional to $Bf_i$ and $Af_j$ respectively. Register 31 stores a count proportional to C. A computer 32 computes the sum, $Af_j - Bf_i + C$. A storage register 33 is updated from computer 32 via a gating matrix 34 operated by a one shot 35. Indicator 22 indicates the number stored in register 33. Computer 32 may cause indicator 22 to read in units of viscosity.

A differentiator 36 resets counters 29 and 30, and computer 32. Computation is initiated by a connection to computer 32 from the "0" output of divider 28, the same also operating one shot 35.

Computer 32 may be a microprocessor, if desired.

OPERATION OF THE CIRCUIT IN FIG. 2

In FIG. 2, counters 29 and 30 with computer 32 are reset at the beginning of one half period of one output of divider 28.

Counters 29 and 30 count $Bf_i$ and $Af_j$, respectively. Counters 29 and 30 count simultaneously during the said one half of the period of one output of divider 28. During the other half period computer calculates $Af_j - Bf_i + C$.

The sum in the computer 32 is transferred to register 33 via circuit 34. One shot 35 operates circuit 34 shortly after computer 32 is turned on via lead 35'.

Figure 3:
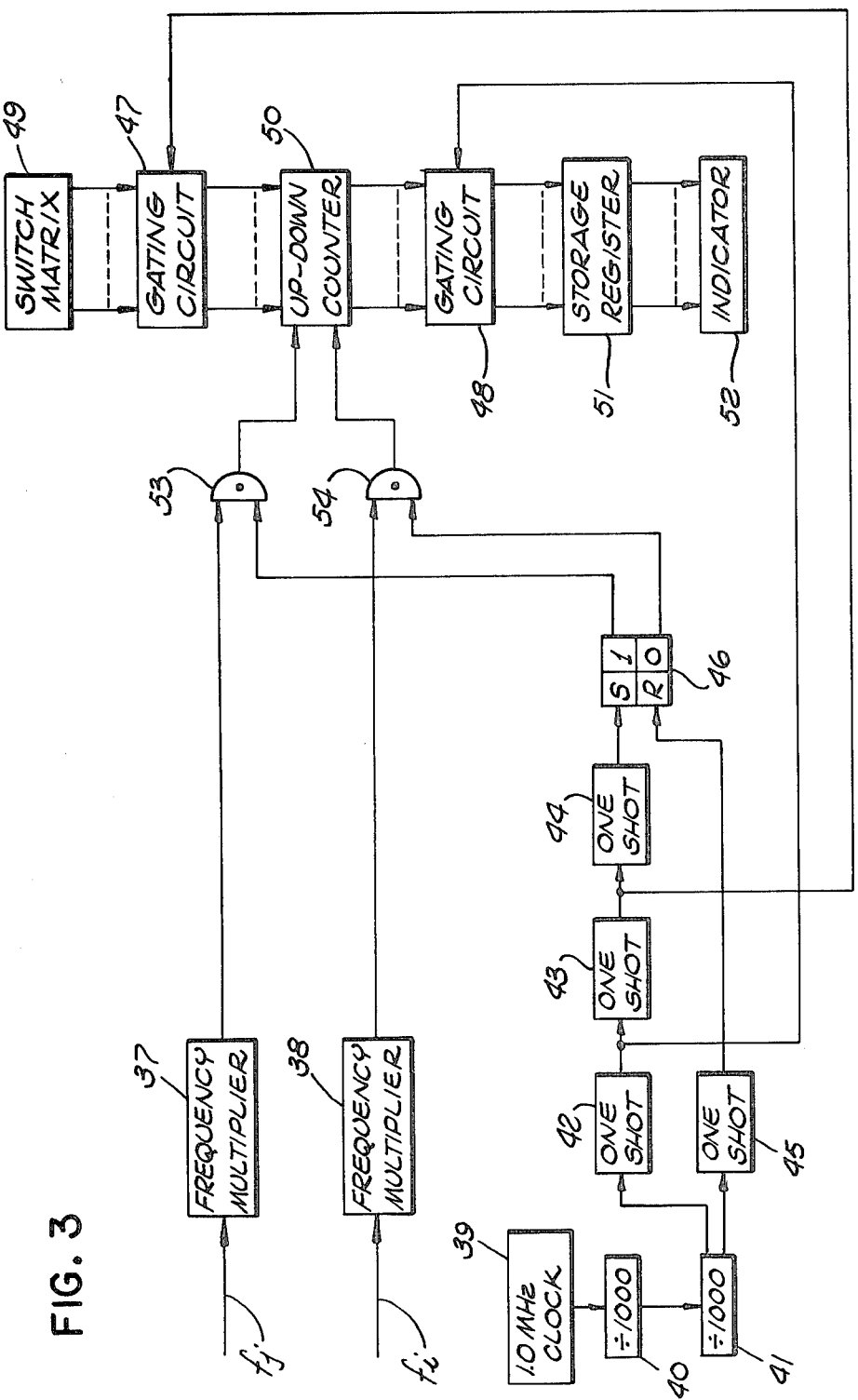
FIG. 3 is a block diagram of an alternative to the output circuit shown in FIG. 2

In FIG. 3, frequency multipliers 37 and 38, clock 39 and dividers 40 and 41 may be identical to those shown in FIG. 2, if desired.

One shots 42, 43, 44 and 45 are provided to operate a flip flop 46 and gating circuits 47 and 48.

A switch matrix 49 is provided with an up-down counter 50, a storage register 51 and an indicator 52.

AND gates 53 and 54 alternately gate $Af_j$ and $Bf_i$, respectively, to counter 50. The periods of one shots 42–45 and the sums thereof are insignificant compared to the period of the outputs of divider 41.

OPERATION OF THE CIRCUIT IN FIG. 3

In FIG. 3, the contents of counter 50 is entered in register 51 by one shot 42 and gating circuit 51. Constant C is then entered in counter 50 by switch maxtix 49 via gating circuit 47, gating circuit 47 being operated by one shot 43. Counter 50 then counts up on receipt of $Af_j$ pulses when AND gate 53 is open, and counts down on receipt of $Bf_i$ pulses when AND gate 54 is open. AND gates 53 and 54 are alternately open because they are respectively connected from the "1" and "0" outputs of flip flop 46.

What is claimed is:

1. A viscosimeter comprising:
a closed loop including first and second turbine flowmeters connected in series, a pump to circulate a fluid through said first and second turbine flowmeters, said first and second turbine flowmeters producing pulses at frequencies $f_i$ and $f_j$, respectively, where the flow rate of fluid through said first and second flowmeters is $Q_i$ and $Q_j$ respectively, where $$Q_i = m_1 f_i + n_1 v + c_1$$

$$Q_j = m_2 f_j + n_2 v + c_2$$

$$Q_i = Q_j$$

where
$m_1$, $n_1$, $c_1$, $m_2$, $n_2$ and $c_2$ are constants and
v is the viscosity of said fluid;
and computer means connected to receive said pulses from both of said first and second turbine flowmeters for producing an output proportional to viscosity v as defined by $$v = Af_j - Bf_i + C,$$

where $$A = m_2/(n_1 - n_2)$$

$$B = m_1/(n_1 - n_2)$$

$$C = (c_2 - c_1)/(n_1 - n_2)$$

and $$n_1 \neq n_2.$$

2. The invention as defined in 1, wherein said closed loop includes an adjustable pump to change the flow-rate of said fluid.

3. The invention as defined in 1, including an indicator for the temperature of said fluid.

4. The invention as defined in 3, including supply means to heat said fluid.

5. The invention as defined in 4, wherein said supply means is controlled with a thermostat.

6. The invention as defined in 5, wherein said thermostat is adjustable.

7. The invention as defined in 6, wherein said computer means includes utilization means connected to receive said output.

8. The invention as defined in 7, wherein said utilization means includes an indicator calibrated in units of viscosity.

9. The invention as defined in 1, wherein said computer means includes utilization means connected to receive said output.

10. The invention as defined in 9, wherein said utilization means includes an indicator calibrated in units of viscosity.

11. A fluid sensitive instrument comprising:
a first turbine flowmeter having a rotor; a pump, a second turbine flowmeter having a rotor; said first and second turbine flowmeters being connected in series with each other and in series with said pump in a closed loop; and computer means for producing an output proportional to the viscosity of a fluid in said closed loop as a function of an angular velocities of said rotors, said turbine flowmeters each having means connected to said computer means for detecting the angular velocity of a respective corresponding rotor.

* * * * *